United States Patent [19]

Matsuo et al.

[11] Patent Number: 4,714,712

[45] Date of Patent: Dec. 22, 1987

[54] CARBOXYLIC ACID ESTERS AND INSECTICIDES CONTAINING THEM AS THE ACTIVE INGREDIENT

[75] Inventors: Noritada Matsuo, Rochester, N.Y.; Kazunori Tsushima, Nishinomiya; Sumio Nishida, Takarazuka; Toshihiko Yano, Ikoma, all of Japan

[73] Assignee: Sumitomo Chemical Company, Limited, Osaka, Japan

[21] Appl. No.: 853,607

[22] Filed: Apr. 18, 1986

[30] Foreign Application Priority Data

Apr. 26, 1985 [JP] Japan .................................. 60-91971
Jun. 4, 1985 [JP] Japan ................................ 60-121233

[51] Int. Cl.[4] ................. C07C 69/743; C07C 69/747; A01N 53/00
[52] U.S. Cl. ...................................... 514/531; 560/124
[58] Field of Search .......................... 560/124; 514/531

[56] References Cited

U.S. PATENT DOCUMENTS

| 4,024,163 | 5/1977 | Elliott | 560/124 |
|---|---|---|---|
| 4,118,505 | 10/1978 | Kitamura | 560/124 |
| 4,243,677 | 1/1981 | Engel | 560/124 |
| 4,252,820 | 2/1981 | Lantzsch | 560/124 |
| 4,362,744 | 12/1982 | Plummer | 560/124 |

FOREIGN PATENT DOCUMENTS

| 0114012 | 7/1984 | European Pat. Off. . |
| 2925315 | 1/1980 | Fed. Rep. of Germany . |
| 2547817 | 12/1984 | France . |
| 55-42045 | 10/1980 | Japan . |
| 1424170 | 2/1976 | United Kingdom . |

OTHER PUBLICATIONS

Elliott, Chem. Soc. Rev., 7 pp. 473-505 (1978).

*Primary Examiner*—Michael L. Shippen

*Attorney, Agent, or Firm*—Stevens, Davis, Miller & Mosher

[57] ABSTRACT

This invention relates to novel carboxylic acid esters represented by the formula (I) below, methods for production thereof and insecticides containing them as the active ingredient, and an alcohol compound useful as an intermediate for manufacturing carboxylic acid esters represented by the formula (I).

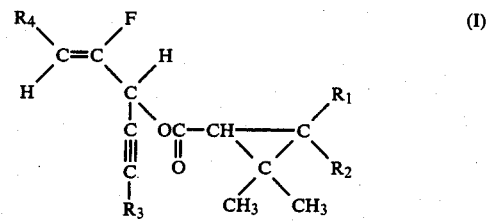

wherein $R_1$ represents a hydrogen atom or a methyl group; when $R_1$ is a hydrogen atom, $R_2$ represents a group of the formula

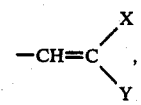

in which X and Y are the same or different and represent a hydrogen atom, a methyl group, a halogen atom or a halogenated lower alkyl group, and when $R_1$ is a methyl group, $R_2$ represents a methyl group; $R_3$ represents hydrogen atom or a methyl group; and $R_4$ represents a hydrogen atom, a lower alkyl group, a lower alkenyl group or a lower alkynyl group.

22 Claims, No Drawings

CARBOXYLIC ACID ESTERS AND INSECTICIDES CONTAINING THEM AS THE ACTIVE INGREDIENT

This invention relates to carboxylic acid esters represented by the formula (I) below, methods for production thereof and insecticides containing them as the active ingredient, and an alcohol compound useful as an intermediate for manufacturing carboxylic acid esters represented by the formula (I),

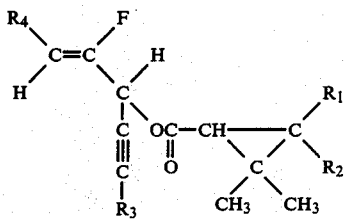

wherein $R_1$ represents a hydrogen atom or a methyl group; when $R_1$ is a hydrogen atom, $R_2$ represents a group of the formula

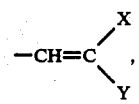

in which X and Y are the same or different and represent a hydrogen atom, a methyl group, a halogen atom (e.g. fluorine, chlorine, bromine) or a halogenated lower alkyl group (e.g. fluorinated, chlorinated or brominated $C_{1-3}$ alkyl), and when $R_1$ is a methyl group, $R_2$ represents a methyl group; $R_3$ represents a hydrogen atom or a methyl group; and $R_4$ represents a hydrogen atom, a lower alkyl group (e.g. $C_{1-5}$ alkyl), a lower alkenyl group (e.g. $C_{2-4}$ alkenyl) or a lower alkynyl group (e.g. $C_{2-4}$ alkynyl).

The inventors of the present invention, after performing studies in order to develop compounds having a superior insecticidal effect, found that the compound of the present invention represented by the above formula (I) has excellent properties as follows.

1. Very rapidly acting on various insects and having a high insecticidal effect
2. Highly effective as an volatile agent or a fumigant
3. Having relatively low toxicity to mammals
4. Exhibiting an excellent effect on insect pests resistant to organophosphorus insecticides or carbamates
5. Can be manufactured at a relatively low cost Although this invention is in a broader sense, included in Japanese published examined patent application No. 42045/1980, no tangible description of the compound of this invention is given in the patent specification. The inventors found that the compound of the present invention represented by the above formula (I), as obviously understood from examples to be described later, has a notably higher insecticidal effect than similar compounds described in said patent application, and thus attained to the present invention.

As specific examples of insect pests against which the compounds of the present invention are particularly effective, there are given for example Diptera such as housefly (*Musca domestica*), common mosquito (*culex pipiens pallens*), etc., Lepidoptera living indoors such as case-bearing clothes moth (*Tinea pellionella*), etc., Dictyoptera such as German cockroach (*Blattella germanica*) and the like. The compound of the present invention are excellently effective against those insects when used as volatile agents or fumigants. The other examples of insect pests against which the compound of the present invention are effective, include Hemiptera such as planthoppers, leafhoppers, aphids, stink bugs, etc., Lepidoptera such as diamondback moth (*Plutella xylostella*), rice stem borer (*Chilo suppressalis*), armywarms, etc., Coleoptera such as dermestid beetles, etc., Orthoptera, and the like.

In the compounds of the present invention represented by the formula (I), preferred compounds are such that $R_1$ and $R_3$ represent hydrogen atoms. More preferred compounds are such that, in the foregoing preferred compounds, X and Y are the same or different and present a methyl group, a chlorine atom, a fluorine atom, a bromine atom or a trifluoromethyl group and $R_4$ represents a $C_{2-4}$ alkyl group, an allyl group or a propargyl group.

The compound of the present invention represented by the above formula (I) can be prepared by reacting a carboxylic acid represented by the formula (II)

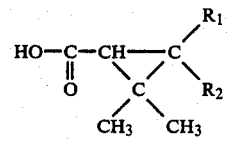

wherein $R_1$ and $R_2$ are as defined above or a reactive derivative thereof with an alcohol compound represented by the formula (III)

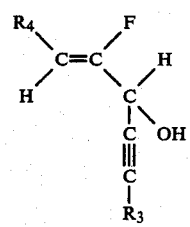

wherein $R_3$ and $R_4$ are as defined above, if necessary, in the presence of a suitable inert solvent, reaction auxiliary reagent or catalyst.

The reactive derivative of the carboxylic acid which is referred to herein include acid halides such as acid chloride, acid bromide, etc., acid anhydrides, and the like.

The compound of the present invention represented by the formula (I) has optical isomers due to the asymmetric carbon atoms on the acid moiety and the alcohol moiety and stereoisomers due to the acid moiety, and all of those isomers are within the scope of the present invention.

In the compound of the present invention, the optical isomers wherein the acid moiety has an absolute configuration of (1R) and/or the alcohol moiety has a levo optical rotation as the corresponding free alcohol have very high insecticidal activities.

In the compound of the present invention, the alcohol moiety has the geometrical configuration of (Z)-form in case of existence of two geometrical isomers at the double bond thereof.

In the following, methods for preparing the compound of the present invention will be described.

Method A

A reaction of a carboxylic acid halide with an alcohol compound.

The desired ester is obtained by reacting an acid halide represented by formula (IV).

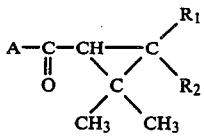 (IV)

wherein A is a halogen atom (e.g. chlorine, bromine), and $R_1$ and $R_2$ are as defined above, preferably an acid chloride, with an alcohol compound represented by the above formula (III) in the presence of a hydrogen halide-removing reagent such as pyridine or triethylamine in an inert solvent at a temperature of $-30°-100°$ C. for 30 minutes to 20 hours.

Method B

A reaction of a carboxylic acid anhydride with an alcohol compound.

The desired ester is obtained by reacting a carboxylic acid anhydride represented by formula (V)

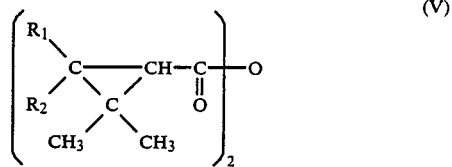 (V)

wherein $R_1$ and $R_2$ are as defined above, with an alcohol compound represented by the above formula (III) in the presence of a base such as pyridine or triethylamine in an inert solvent such as benzene, toluene, hexane or acetone at a temperature of $-20°$ C.$-100°$ C. for 1 to 20 hours.

Method C

A dehydrating reaction between a carboxylic acid and an alcohol compound.

The desired ester is obtained by reacting a carboxylic acid represented by the above formula (II) with an alcohol represented by formula (III) in the presence of dehydrating agent such as dicyclohexyl carbodiimide at a temperature of $0°-150°$ C. for 30 minutes to 10 hours.

The compound obtained by the above methods can be purified, if necessary by means of chromatography or distillation.

The compound of the present invention prepared according to the above methods are exemplified in Table 1.

However, this invention is not limited to those examples.

TABLE 1

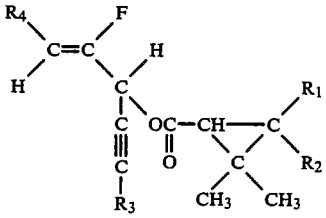

| Compound No. | $R_1$ | $R_2$ | $R_3$ | $R_4$ | Acid moiety | Alcohol moiety | Physical Property ($\eta_D(°C.)$) |
|---|---|---|---|---|---|---|---|
| (1) | H | Cl\C=CH—/Cl | H | $C_2H_5$ | (1R)-trans | (±) | 1.4930 (25.5) |
| (2) | H | CH$_3$\C=CH—/CH$_3$ | H | $C_2H_5$ | (1R)-trans | (±) | 1.4709 (27.0) |
| (3) | H | Cl\C=CH—/Cl | H | $C_2H_5$ | (1RS)-cis, trans | (±) | 1.4913 (26.5) |
| (4) | H | Cl\C=CH—/Cl | H | HC≡C—CH$_2$— | (1R)-trans | (±) | 1.5083 (22.5) |
| (5) | H | CH$_3$CH=CH— | H | $C_2H_5$ | (1R)-trans | (±) | 1.4722 (22.5) |

TABLE 1-continued

Structure with R4, F, H, C=C, OC-CH, R1, R2, CH3, CH3, R3 substituents on cyclopropane ester with alkyne.

| Compound No. | R1 | R2 | R3 | R4 | Acid moiety | Alcohol moiety | Physical Property ($\eta_D$(°C.)) |
|---|---|---|---|---|---|---|---|
| (6) | H | F, F, C=CH— | H | HC≡C—CH$_2$— | (1R)-trans | (±) | 1.4490 (23.0) |
| (7) | H | Cl, Cl, C=CH— | H | n-C$_3$H$_7$— | (1R)-trans | (±) | 1.4888 (23.5) |
| (8) | H | CH$_3$, CH$_3$, C=CH— | H | i-C$_3$H$_7$— | (1R)-trans | (±) | 1.4661 (24.5) |
| (9) | H | Cl, Cl, C=CH— | H | H$_2$C=CH—CH$_2$— | (1RS)-trans | (±) | 1.5002 (25.5) |
| (10) | H | Cl, Cl, C=CH— | H | HC≡C—CH$_2$CH$_2$— | (1R)-trans | (±) | 1.5076 (24.5) |
| (11) | CH$_3$ | CH$_3$ | H | HC≡C—CH$_2$— | — | (±) | 1.4875 (24.5) |
| (12) | H | Cl, Cl, C=CH— | CH$_3$ | C$_2$H$_5$— | (1R)-trans | (±) | 1.4941 (23.5) |
| (13) | H | Cl, CF$_3$, C=CH— | H | C$_2$H$_5$ | (1RS)-trans | (±) | 1.4680 (23.5) |
| (14) | H | CH$_3$, CH$_3$, C=CH— | H | HC≡C—CH$_2$— | (1R)-trans | (±) | 1.4884 (22.5) |
| (15) | H | Cl, Cl, C=CH— | H | C$_2$H$_5$ | (1RS)-cis | (±) | 1.4972 (21.5) |
| (16) | H | Cl, CH$_3$, C=CH— | H | C$_2$H$_5$ | (1RS)-trans | (±) | 1.4826 (21.0) |
| (17) | H | Cl, Cl, C=CH— | H | C$_2$H$_5$ | (1R)-trans | (−) | 1.4947 (24.0) |

TABLE 1-continued

[Structure diagram showing a cyclopropane ester with vinyl substituent bearing R4 and F, cyclopropane carbons bearing R1, R2, and gem-dimethyl groups, with OC(=O)CH-C≡C-R3 acid moiety]

| Compound No. | R$_1$ | R$_2$ | R$_3$ | R$_4$ | Acid moiety | Alcohol moiety | Physical Property ($\eta_D$(°C.)) |
|---|---|---|---|---|---|---|---|
| (18) | H | Cl\C=CH—/CF$_3$ | H | C$_2$H$_5$ | (1RS)-cis | (±) | 1.4539 (23.0) |
| (19) | H | Cl\C=CH—/Cl | H | n-C$_3$H$_7$ | (1RS)-cis, trans | (±) | 1.4918 (25.5) |
| (20) | H | Cl\C=CH—/Cl | H | i-C$_3$H$_7$ | (1RS)-cis, trans | (±) | 1.4868 (25.5) |

(*) Examples of the substituent R$_1$, R$_2$, R$_3$ and R$_4$ and explanations of isomerism on the acid moiety and the alcohol moiety of the compound represented by the formula (I).

The compound of the present invention will be described in more detail according to the following examples.

EXAMPLE 1

Production of compound (1) by method (A)

After 1.28 g (0.01 mole) of (Z)-3-hydroxy-4-fluoro-4-hepten-1-yne and 2.27 g (0.01 mole) of (1R)-trans-2,2-dimethyl-3-(2,2-dichlorovinyl)-cyclopropane-1-carboxylic acid chloride were dissolved in 50 ml of dry toluene, 1.58 g (0.02 mole) of pyridine was added to the solution dropwise while it was being cooled with ice. After the addition of pyridine, the mixture was stirred at room temperature for 5 hours to complete the reaction. The reaction solution was poured into 50 ml of ice water and then the toluene layer was separated. Next, the separated toluene layer was successively washed with 5% dilute hydrochloric acid, saturated aqueous sodium bicarbonate solution and saturated aqueous sodium chloride solution. Next, after the toluene layer was dried over anhydrous sodium sulfate, toluene was distilled off to obtain a residue. The residue was passed through a column packed with 50 g of silica gel by using a mixed solvent composed of ethyl acetate and n-hexane in a ratio of 1 to 20 as an eluent, thereby obtaining 2.68 g of the desired ester as a colorless oily substance.

Yield: 84.0% v.s. the theoretical yield based on the carboxylic acid chloride used.

EXAMPLE 2

Production of compound (2) by method (B)

After 1.59 g of (1R)-trans-2,2-dimethyl-3-(2-methyl-1-propenyl)-cyclopropanecarboxylic acid anhydride (5 m moles) and 0.32 g of (Z)-3-hydroxy-4-fluoro-4-hepten-1-yne (2.5 m moles) were dissolved in 20 ml of dry toluene, 0.50 g of triethylamine (5 m moles) was added to the solution and the mixture was stirred at 40° C. for 10 hours. Next, after the reaction solution was poured into 50 ml of ice water, the toluene layer was collected and the aqueous layer was extracted with 20 ml of toluene. The toluene layers were combined and washed twice each with 20 ml of 5% aqueous sodium carbonate solution. The toluene layer was successively washed with 5% dilute hydrochloric acid, saturated aqueous sodium bicarbonate solution and saturated aqueous sodium chloride solution. The toluene solution was dried over anhydrous magnesium sulfate. After the solvent was distilled off, the residue was passed through a column packed with 50 g of silica gel by using a mixed solvent composed of ethyl acetate and n-hexane in a ratio of 1 to 20 as an eluent, thereby obtaining 0.50 g of the desired ester.

Yield: 72% v.s. the theoretical yield based on the alcohol used.

EXAMPLE 3

Production of compound (13) by method (C)

After 0.64 g of (Z)-3-hydroxy-4-fluoro-4-hepten-1-yne (5 m moles) and 1.21 g of (1RS)-trans-2,2-dimethyl-3-(2-chloro-2-trifluoronethylvinyl)-cyclopropane-1-carboxylic acid (5 m moles) were dissolved in 20 ml of dry dichloromethane, 2.06 g of dicyclohexylcarbodiimide (10 m moles) was added thereto and the mixture was left over night. On the next day, after the mixture was heated to reflux for four hours to complete the reaction, the mixture was cooled to deposit dicyclohexylurea which was then subjected to filtration. The thus prepared filtrate was then concentrated to obtain an oily substance. Then, the oily substance was passed through a column packed with 60 g of silica gel by using a mixed solvent composed of ethyl acetate and n-hexane in a ratio of 1 to 20 as an eluent, thereby obtaining 1.09 g of the desired ester as a colorless oily substance.

Yield: 62.0% v.s. the theoretical yield based on the carboxylic acid used.

EXAMPLE 4

Production of compound (17) by method (A)

After 235 mg of (−)-(Z)-3-hydroxy-4-fluoro-4-hepten-1-yne was dissolved in 5 ml of dry toluene, 200 mg of pyridine was added thereto. Next, into the mixture was added 390 mg of (1R)-trans-2,2-dimethyl-3-(2,2-dichlorovinyl)-cyclopropane-1-carboxylic acid chloride while being cooled with ice water and then the mixture was stirred at 20° C. for 10 hours. The reaction mixture was subjected to the same after-treatment as in Example 1, thereby obtaining 490 mg of the desired ester.

EXAMPLE 5

Production of compound (18) by method (A)

After 250 mg (2.0 m mole) of (Z)-3-hydroxy-4-fluoro-4-hepten-1-yne and 500 mg (1.9 m mole) of (1RS)-cis-2,2-dimethyl-3-(2-chloro-2-trifluoromethylvinyl)-cyclopropane-1-carboxylic acid chloride were dissolved in 10 ml of dry toluene, 320 mg (4.0 m mole) of pyridine was added to the solution dropwise while it was being cooled with ice. After the addition of pyridine, the mixture was stirred at room temperature for 5 hours to complete the reaction. The reaction solution was poured into 20 ml of 5% diluted hydrochloric acid cooled with ice and then the toluene layer was separated. The aqueous layer was extracted with 5 ml of ethyl acetate twice and the ethyl acetate layer was combined with the above toluene layer. Next, those obtained organic solvent layer was successively washed with saturated aqueous sodium bicarbonate solution and saturated aqueous sodium chloride solution, and then dried over anhydrous sodium sulfate. The organic layer was concentrated to obtain a residue. The residue was passed through a column packed with 17 g of silica gel by using a mixed solvent composed of ethyl acetate and n-hexane in a ratio of 1 to 20 as an eluent, thereby obtaining 480 mg of the desired ester as a colorless oil.

Yield: 71.0% v.s. the theoretical yield based on the carboxylic acid chloride used.

EXAMPLE 6

Production of compound (19) by method (A)

After 1.0 g (7.0 m mole) of (Z)-3-hydroxy-4-fluoro-4-octen-1-yne and 1.46 g (6.4 m mole) of (1RS)-cis, trans-2,2-dimethyl-3-(2,2-dichlorovinyl)-cyclopropane-1-carboxylic acid chloride were dissolved in 30 ml of dry toluene, 840 mg (11 m mole) of pyridine was added to the solution dropwise while it was being cooled with ice. After the addition of pyridine, the mixture was stirred at room temperature for 6 hours to complete the reaction. The reaction solution was poured into 40 ml of 5% diluted hydrochloric acid cooled with ice and then the toluene layer was separated. The aqueous layer was extracted with 10 ml of ethyl acetate twice and the ethyl acetate layer was combined with the above toluene layer. Next, those obtained organic solvent layer was successively washed with saturated aqueous sodium bicarbonate solution and saturated aqueous sodium chloride solution, and then dried over anhydrous sodium sulfate. The organic layer was concentrated to obtain a residue. The residue was passed through a column packed with 60 g of silica gel by using a mixed solvent composed of ethyl acetate and n-hexane in a ratio of 1 to 20 as an eluent, thereby obtaining 1.8 g of the desired ester as a colorless oil.

Yield: 84.5% v.s. the theoretical yield based on the carboxylic acid chloride used.

EXAMPLE 7

Production of compound (20) by method (A)

After 1.0 g (7.0 m mole) of (Z)-3-hydroxy-4-fluoro-6-methyl-4-hepten-1-yne and 1.5 g (6.6 m mole) of (1RS)-cis, trans-2,2-dimethyl-3-(2,2-dichlorovinyl)-cyclopropane-1-carboxylic acid chloride were dissolved in 30 ml of dry toluene, 900 mg (12 m mole) of pyridine was added to the solution dropwise while it was being cooled with ice. After the addition of pyridine, the mixture was stirred at room temperature for 6 hours to complete the reaction. The reaction solution was poured into 40 ml of 5% diluted hydrochloric acid cooled with ice and then the toluene layer was separated. The aqueous layer was extracted with 10 ml of ethyl acetate twice and the ethyl acetate layer was combined with the above toluene layer. Next, thus combined organic solvent layer was successively washed with saturated aqueous sodium bicarbonate solution and saturated aqueous sodium chloride solution, and then dried over anhydrous sodium sulfate. The organic layer was concentrated to obtain a residue. The residue was passed through a column packed with 60 g of silica gel by using a mixed solvent composed of ethyl acetate and n-hexane in a ratio of 1 to 20 as an eluent, thereby obtaining 2.1 g of the desired ester as a colorless oil.

Yield: 97.1% v.s. the theoretical yield based on the carboxylic acid chloride used.

EXAMPLE 8

Production of compound (3) by method (A)

After 1.28 g (0.01 mole) of (Z)-3-hydroxy-4-fluoro-4-hepten-1-yne and 2.39 g (0.0105 mole) of (1RS)-cis, trans-2,2-dimethyl-3-(2,2-dichlorovinyl)-cyclopropane-1-carboxylic acid chloride were dissolved in 60 ml of dry benzene, 1.52 g (0.015 mole) of triethylamine was added to the solution dropwise while it was being cooled with ice. After the addition of triethylamine, the mixture was stirred at 40° C. for 5 hours to complete the reaction. The reaction solution was poured into 50 ml of ice water and then the benzene layer was separated. Next, the separated benzene layer was successively washed with 5% dilute hydrochloric acid, saturated aqueous sodium bicarbonate solution and saturated aqueous sodium chloride solution. Next, after the benzene layer was dried over anhydrous sodium sulfate, toluene was distilled off to obtain a residue. The residue was passed through a column packed with 50 g of silica gel by using a mixed solvent composed of ethyl acetate and n-hexane in a ratio of 1 to 20 as an eluent, thereby obtaining 2.59 g of the desired ester as a colorless oily substance.

Yield: 81.2% v.s. the theoretical yield based the alcohol compound used.

Example 9

Production of compound (1) by method (A)

After 1.28 g (0.01 mole) of (Z)-3-hydroxy-4-fluoro-4-hepten-1-yne and 2.16 g (0.0095 mole) of (1R)-trans-2,2-dimethyl-3-(2,2-dichlorovinyl)-cyclopropane-1carboxylic acid chloride were dissolved in 70 ml of hexane, 1.58 g (0.02 mole) of pyridine was added to the solution dropwise while it was being cooled with ice. After the addition of pyridine, the mixture was stirred at room temperature for 10 hours to complete the reaction. The reaction solution was poured into 50 ml of ice water and then the hexane layer was separated. Next, the separated hexane layer was successively washed with 5% dilute hydrochloric acid, saturated aqueous sodium bicarbonate solution and saturated aqueous sodium chloride solution. Next, after the toluene layer was dried over anhydrous sodium sulfate, toluene was distilled off to obtain a residue. The residue was passed through a column packed with 50 g of silica gel by using a mixed solvent composed of ethyl acetate and n-hexane in a ratio of 1 to 20 as an eluent, thereby obtaining 2.31 g of the desired ester as a colorless oily substance.

Yield: 76.2% v.s. the theoretical yield based on the carboxylic acid chloride used.

EXAMPLE 10

Production of compound (2) by method (A)

After 1.28 g (0.01 mole) of (Z)-3-hydroxy-4-fluoro-4-hepten-1-yne and 1.58 g (0.02 mole) of pyridine were dissolved in 50 ml of dry toluene, 1.87 g (0.01 mole) of (1R)-trans-2,2-dimethyl-3-(2-methyl-1-propenyl)-cyclopropane-1-carboxylic acid chloride was added to the solution dropwise while it was being cooled with ice. Then, the mixture was stirred at room temperature for 20 hours to complete the reaction. The reaction solution was poured into 5 ml of ice water and then the toluene layer was separated. Next, the separated toluene layer was successively washed with 5% dilute hydrochloric acid, saturated aqueous sodium bicarbonate solution and saturated aqueous sodium chloride solution. Next, after the toluene layer was dried over anhydrous sodium sulfate, toluene was distilled off to obtain a residue. The residue was passed through a column packed with 50 g of silica gel by using a mixed solvent composed of ethyl acetate and n-hexane in a ratio of 1 to 20 as an eluent solvent, thereby obtaining 2.45 g of the desired ester as a colorless oily substance.

Yield: 88.0% v.s. the theoretical yield based on the carboxylic acid chloride used.

EXAMPLE 11

Production of compound (3) by method (B)

After 2.00 g of (1RS)-cis, trans-2,2-dimethyl-3-(2,2-dichlorovinyl)-cyclopropanecarboxylic acid anhydride (5 m moles) and 0.32 g of (Z)-3-hydroxy-4-fluoro-4-hepten1-yne (2.5 m moles) were dissolved in 20 ml of dry toluene, 0.79 g of pyridine (10 m moles) was added to the solution and the mixture was stirred at 50° C. for 20 hours. Next, after the reaction solution was poured into 50 ml of ice water, the toluene layer was collected and the aqueous layer was extracted with 20 ml of toluene. The thus prepared toluene layers were combined and washed twice each with 20 ml of 5% aqueous sodium carbonate solution. The toluene layer was then successively washed with 5% dilute hydrochloric acid, saturated aqueous sodium bicarbonate solution and saturated aqueous sodium chloride solution. The toluene solution was dried over anhydrous magnesium sulfate. Next, after the solvent was distilled off, the residue was passed through a column packed with 50 g of silica gel by using a mixed solvent composed of ethyl acetate and n-hexane in a ratio of 1 to 20 as an eluent, thereby obtaining 0.62 g of the desired ester.

Yield: 77.7% v.s. the theoretical yield based on the alcohol used.

EXAMPLE 12

Production of compound (3) by method (C)

After 0.64 g of (Z)-3-hydroxy-4-fluoro-4-hepten-1-yne (5 m moles) and 1.05 g of (1RS)-cis, trans-2,2-dimethyl-3-(2,2-dichlorovinyl)-cyclopropane-1-carboxylic acid (5 m moles) were dissolved in 20 ml of dry benzene, 2.06 g of dicyclohexylcarbodiimide (10 m moles) was added thereto and the mixture was left over night. On the next day, after the mixture was heated to reflux for two hours to complete the reaction, the mixture was cooled to deposit dicyclohexylurea which was then subjected to filtration. The thus prepared filtrate was then concentrated to obtain an oily substance. After that, the oily substance was passed through a column packed with 60 g of silica gel by using a mixed solvent composed of ethyl acetate and h-hexane in a ratio of 1 to 20 as an eluent, thereby obtaining 1.21 g of the desired ester as a colorless oily substance.

Yield: 75.9% v.s. the theoretical yield based on the carboxylic acid used.

The alcohol compound represented by the above formula (III) is a novel compound. They can be prepared from corresponding aldehydes, for example, according to the following synthetic route.

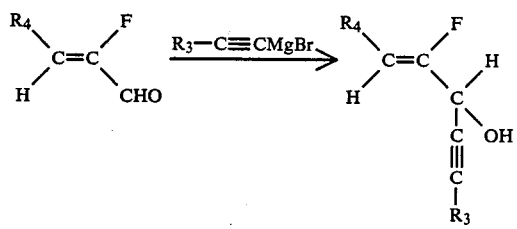

wherein $R_3$ and $R_4$ are as described above.

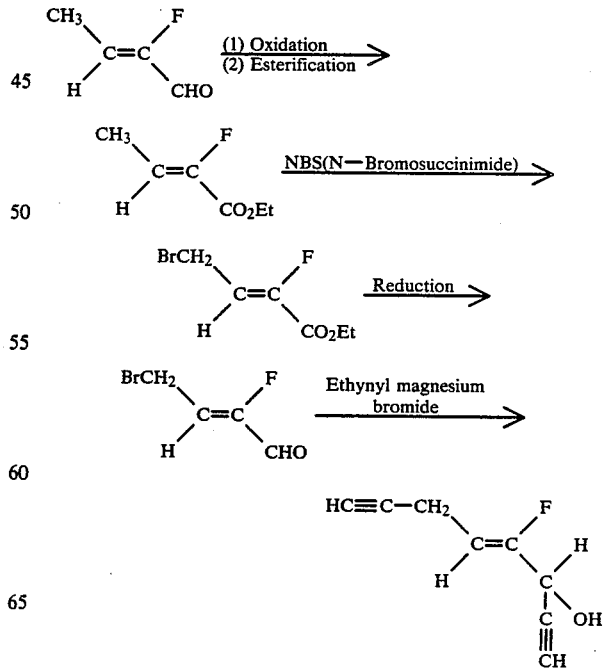

In the above methods, aldehyde compounds used as starting materials can be produced according to the methods described on page 3387 of Tetrahedron letters Vol. 24 (1983) and on page 1739 of Helvetica Chimica Acta Vol. 60 (1977).

In the following reference examples, synthetic examples of alcohols represented by the formula (III) will be described.

Reference example 1. (Synthesis of ethyl 2-fluorocrotonate)

After 4 g of (Z)-2-fluorocrotyl aldehyde was dissolved in 10 ml of acetone, 45 g of Jones reagent was added into the solution dropwise at 20° C. or below while the solution was cooled with ice water. After this reaction solution was stirred at 20° C. for one hour, 10 ml of isopropyl alcohol was added dropwise thereto. After the mixture was stirred, ice water was added to the reaction solution and then the mixture was extracted with diethyl ether twice. The ether layer was then washed with aqueous saturated sodium chloride solution and dried over anhydrous magnesium sulfate and then concentrated, thereby obtaining 3.5 g of a corresponding carboxylic acid. To the carboxylic acid were added 10 ml of dimethylformamide, 3.6 g of ethyl bromide and 3.3 g of triethylamine and the mixture was stirred at 20° C. for 24 hours. After this reaction solution was poured into ice water, the mixture was extracted with ethyl acetate twice. The ethyl acetate layer was successively washed with water and aqueous saturated sodium chloride solution and then concentrated to give a residue. The residue was subjected to distillation in vacuo, thereby obtaining 2.8 g of the desired compound.

Boiling point: 75°–82° C./95 mmHg
$\eta_D$(°C.): 1.4702 (24° C.)
NMR data (CDCl$_3$) δ
1.29 (t, 3H, J=8 Hz);
1.77 (dd, 3H, J=3 Hz, 8 Hz);
4.23 (q, 2H);
5.7–6.6 (dq, 1H, J=8 Hz, 33 Hz);

REFERENCE EXAMPLE 2

(Synthesis of (Z)-ethyl 4-bromo-2-fluorocrotonate)

After 9.0 g of (Z)-ethyl 2-fluorocrotonate was dissolved in 60 ml of carbon tetrachloride, 13.5 g of N-bromosuccinimide and 10 mg of benzoyl peroxide were added thereto. The mixture was heated to reflux for 6 hours. This reaction solution was filtered and the filtrate was concentrated to give a residue. The residue was subjected to silica gel column chromatography (eluent; n-hexane:ethyl acetate=20:1), thereby obtaining 8.5 g of the desired compound.

NMR data (CDCl$_3$) δ
1.36 (t, 3H, J=8 Hz);
5.0, 4.15 (dd, 2H, J=9 Hz, 2 Hz);
4.35 (q, 2H, J=8 Hz);
6–6.8 (dt, 1H, J=9 Hz, 30 Hz).

REFERENCE EXAMPLE 3

(Synthesis of (Z)-4-bromo-2-fluorocrotyl aldehyde)

After 3.0 g of (Z)-ethyl 4-bromo-2-fluorocrotonate was dissolved in 30 ml of dichloromethane, a solution of diisobutyl aluminum halide in n-hexane (the molar amount of diisobutyl aluminum was 1.3 times that of the above ester) was added to the solution dropwise while it was maintained at −60° C. After the mixture was stirred at the same temperature for 30 minutes, the reaction solution was poured into cooled 10% dilute hydrochloric acid. The dichloromethane layer was separated and the aqueous layer was extracted with dichloromethane. The thus obtained dichloromethane layers were combined and washed with aqueous saturated sodium chloride solution. The dichloromethane layer was dried over anhydrous magnesium sulfate, thereby obtaining 2.5 g of desired compound as a pale yellow oily substance.

NMR data (CDCl$_3$) δ
4.1–4.3 (m, 2H);
5.9, 6.4 (dt, 1H, J=8 Hz, 30 Hz);
9.13, 9.44 (d, 1H, J=20 Hz).

REFERENCE EXAMPLE 4

(Synthesis of (Z)-3-hydroxy-4-fluoro oct-4-en-1,7-diyne)

After 2.5 g of (Z)-4-bromo-2-fluorocrotyl aldehyde was dissolved in 20 ml of dry tetrahydrofurane, a tetrahydrofurane solution of acetylene magnesium bromide (the molar amount of acetylene magnesium bromide was 4 times that of the said aldehyde) was added to the solution dropwise while it was maintained at 0° C. After the mixture was stirred at 20° C. for 12 hours, 200 mg of cuprous chloride was added thereto and then the mixture was heated to reflux for 6 hours. The reaction solution was poured into 100 ml of dilute hydrochloric acid cooled with ice, and then the mixture was extracted with ethyl acetate twice. The ethyl acetate layer was washed with saturated aqueous sodium chloride solution and dried over anhydrous magnesium sulfate, and then concentrated to give a residue. The residue was subjected to silica gel chromatography eluent; n-hexane:ethyl acetate=3:1), thereby obtaining 1.1 g of the desired compound as a pale yellow oil.

$\eta_D$(°C.): 1.4769 (23.0° C.)
NMR data (CDCl$_3$) δ
2.03 (t, 1H, J=3 Hz);
2.65 (d, 1H, J=2 Hz);
3.1 (m, 2H);
3.8–5.0 (bd, 1H);
5.05, 5.6 (dt, 1H, J=8 Hz, 32 Hz).

REFERENCE EXAMPLE 5

(Synthesis of (Z)-3-hydroxy-4-fluoro-4-hepten-1-yne)

After 13.0 g of (Z)-2-fluoro-2-pentenal was dissolved in 30 ml of dry tetrahydrofurane, a tetrahydrofurane solution of acetylene magnesium bromide (the molar amount of acetylene magnesium bromide was 1.5 times that of the said aldehyde) was added to the solution dropwise while it was cooled with ice and maintained at a temperature of 10° C. or below. The mixture was stirred for 30 minutes while being cooled with ice and then stirred at 20° C. for one hour. The reaction solution was poured into ice-cooled 5% dilute hydrochloric acid and extracted with ethyl acetate. The ethyl acetate layer was washed with saturated aqueous sodium chloride solution and dried over anhydrous magnesium sulfate. After the solvent was distilled off, the residue was distilled under reduced pressure, thereby obtaining 9.5 g of the desired substance as a pale yellow oil.

Boiling point: 85°–92° C./30 mmHg
NMR data (CDCl$_3$) δ
1.00 (t, 3H, J=8 Hz);
1.8–2.2 (m, 2H);
2.56 (d, 1H, 2.5 Hz);

4.8, 5.4 (dt, 1H, J=8 Hz, 36 Hz);
4.7, 4.9 (dd, 1H, J=2.5 Hz, 12 Hz);

REFERENCE EXAMPLE 6

(Synthesis of
(−)-(Z)-3-hydroxy-4-fluoro-4-hepten-1-yne)

After 1.0 g of (±)-(Z)-3-hydroxy-4-fluoro-4-hepten-1yne and 1.4 g of the lactone of (1R)-cis-3,3-dimethyl-2-(dihydroxymethyl)-cyclopropanecarboxylic acid were dissolved in 50 ml of benzene, 20 mg of p-toluenesulfonic acid was added to the solution. The mixture was heated to reflux for 12 hours while the water was separated off. The reaction solution was washed with 2% aqueous potassium carbonate solution and concentrated to give a residual oil. The oil was subjected to preparative a thin layer chromatography [developed three times and used 8 pieces of plate of Merck Kieselgel Art. 13792 (eluent; n-hexane: diethyl ether =4:1)]. Of the two diastereoisomers located in upper and the lower areas on the plate, the one with a lower Rf value was scraped off and then eluted with ethyl acetate. Thus obtained eluent was concentrated to obtain 510 mg of the lactone of 2-[(4-fluoro-4-hepten-1-yn-3-yloxy)-hydroxymethyl]-3,3-dimethylcyclopropanecarboxylic acid as an oil. To oil were added 10 ml of methanol and 10 mg of p-toluenesulfonic acid and then the mixture was left for 10 hours at room temperature. After that, methanol was distilled off and the residual oil was subjected to silica gel column chromatography (eluent; n-hexane : ethyl acetate =10:1), thereby obtaining 235 mg of the desired (−)-(Z)-3-hydroxy-4-fluoro-4-hepten-1-yne.

$[\alpha]_D^{23} = -34.4°$ (C=0.57, chloroform)

The thus obtained alcohol was converted into the ester of 2-methoxy-2-trifluoromethylphenylacetic acid. HPLC analysis (column, Lichrosorb SI-60 4 mm×30 cm, eluent; n-hexane : ethyl acetate =500:2) of this ester indicated that it was composed of (−)-isomer and (+)-isomer in a ratio of 96 to 4.

When the compounds of the present invention are used as an active ingredient for an insecticidal composition, they may be used as it is without adding any other ingredients. Generally, however, they are formulated into emulsifiable concentrates, wettable powders, dusts, granules, oil sprays, aerosols, heating fumigants (e.g. mosquito coils, electric mosquito mats), foggings, non-heating fumigants (e.g. insecticidal sheets, insecticidal strip), poisonous baits, etc. by mixing with solid carriers, liquid carriers, gaseous carriers, surface active agents, other auxiliaries for formulation, baits, etc., or impregnating into bases such as mosquito coil carrier, mat, etc.

These preparations contain 0.001 to 95% by weight of the present compound as an active ingredient.

The solid carrier includes for example fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide and the like. Furthermore, in case of mat preparations, the solid carrier includes a ceramic plate, a sheet of asbestos, pulp plate and the like. The liquid carrier includes for example aliphatic hydrocarbons (e.g. kerosene, light mineral oils), aromatic hydrocarbons (e.g. benzene, toluene, xylene, methylnaphthalene), halogenated hydrocarbons e.g. dichloromethane, trichloroethane, carbon tetrachloride), alcohols (e.g. methanol, ethanol, isopropanol, ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil) and the like. The gaseous carrier includes for example freon gas, LPG (liquefied petroleum gas), dimethyl ether and the like. The surface active agent used for emulsification, disersion, wetting, etc. includes for example anionic surface active agents such as the salt of alkyl sulfates, alkyl(aryl) sulfonates, dialkyl sulfosuccinates, the salt of polyoxyethylene alkylaryl ether phosphoric acid ester, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The adjuvants for formulation such as sticking agents, dispersing agents, etc. includes for example lignosulfonates, alginates, polyvinyl alcohol, gum arabic, molasses, casein, gelatin, CMC (carboxymethyl cellulose), pine oil, agar, etc. The stabilizer includes for example alkyl phosphates [e.g. PAP (isopropyl acid phosphate), TCP (tricresyl phosphate)], vegetable oils, epoxidized oil, the foregoing surface active agents, antioxidants (e.g. BHT, BHA), fatty acid salts (e.g. sodium oleate, calcium stearate), fatty acid esters (e.g. methyl oleate, methyl stearate) and the like.

Next, Formulation Examples will be shown. The present compounds are shown by Compound No. described in Table 1. Parts in the examples are by weight.

FORMULATION EXAMPLE 1

One part of each of the present compounds (1) to (20) and 99 parts of kerosene are mixed to obtain an oil spray of each compound.

FORMULATION EXAMPLE 2

0.5 Part of each of the present compounds (1) to (20) and 99.5 parts of kerosene are mixed to obtain an oil spray of each compound.

FORMULATION EXAMPLE 3

0.2 Part of each of the present compounds (1) to (20) and 99.8 parts of kerosene are mixed to obtain an oil spray of each compound.

FORMULATION EXAMPLE 4

0.1 Part of each of the present compounds (1) to (20) and 99.9 parts of kerosene are mixed to obtain an oil spray of each compound.

FORMULATION EXAMPLE 5

0.2 Part of each of the present compounds (1) to (20), 1 part of piperonyl butoxide and 98.8 parts of kerosene are mixed to obtain an oil spray of each compound.

FORMULATION EXAMPLE 6

0.1 Part of each of the present compounds (1) to (20), 0.5 part of piperonyl butoxide and 99.4 part of kerosene are mixed to obtain an oil spray of each compound.

FORMULATION EXAMPLE 7

10 Parts of each of the present compounds (1) to (20), 14 parts of polyoxyethylene styrylphenyl ether, 6 parts of calcium dodecylbenzenesulfonate and 70 parts of xylene are well mixed to obtain an emulsifiable concentrate of each compound.

FORMULATION EXAMPLE 8

5 Parts of each of the present compounds (1) to (20), 20 parts of fenitrothion, 21 parts of polyoxyethylene styrylphenyl ether, 9 parts of calcium dodecylbenzenesulfonate and 45 parts of xylene are well mixed to obtain an emulsifiable concentrate of each compound.

FORMULATION EXAMPLE 9

20 Parts of each of the present compounds (1) to (20), 10 parts of fenitrothion, 3 parts of calcium lignosulfonate, 2 parts of sodium lauryl sulfate and 65 parts of synthetic hydrated silicon dioxide are well pulverized and mixed together to obtain a wettable powder of each compound.

FORMULATION EXAMPLE 10

One part of each of the present compounds (1) to (20), 2 parts of carbaryl, 87 parts of kaolin clay and 10 parts of talc are well pulverized and mixed together to obtain a dust formulation of each compound.

FORMULATION EXAMPLE 11

5 Parts of each of the present compounds (1) to (20), 1 part of synthetic hydrated silicon dioxide, 2 parts of calcium lignosulfonate, 30 parts of bentonite and 62 parts of kaolin clay are well pulverized and mixed thoroughly, kneaded well with water, granulated and then dried to obtain granules of each compound.

FORMULATION EXAMPLE 12

0.4 Part of each of the present compounds (1) to (20) and 49.6 parts of deodorized kerosene are well mixed into a solution. The solution is filled in an aerosol container, and after attaching a valve portion to the container, 50 parts of a propellant (liquefied petroleum gas) is charged therein through the valve under pressure to obtain an oil-based aerosol of each compound.

FORMULATION EXAMPLE 13

0.2 Part of each of the present compounds (1) to (20), 1 part of piperonyl butoxide and 48.8 parts of deodorized kerosene are well mixed into a solution. The solution is filled in an aerosol container, followed by the procedures described in Formulation Example 12, to obtain an oil-based aerosol of each compound.

FORMULATION EXAMPLE 14

0.2 Part of each of the present compounds (1) to (20), 0.2 part of d-phenothrin and 49.6 parts of deodorized kerosene are well mixed into a solution. The solution is filled in an aerosol container, followed by the procedures described in Formulation Example 12, to obtain an oil-based aerosol of each compound.

FORMULATION EXAMPLE 15

0.2 Part of each of the present compounds (1) to (20), 0.05 part of d-resmethrin and 49.75 parts of deodorized kerosene are well mixed into a solution. The solution is filled in an aerosol container, followed by the procedures described in Formulation Example 12, to obtain an oil-based aerosol of each compound.

FORMULATION EXAMPLE 16

0.2 Part of each of the present compounds (1) to (20), 0.4 part of permethrin and 49.4 parts of deodorized kerosene are well mixed into a solution. The solution is filled in an aerosol container, followed by the procedures described in Formulation Example 12, to obtain an oil-based aerosol of each compound.

FORMULATION EXAMPLE 17

0.2 Part of each of the present compounds (1) to (20), 0.2 part of d-cyphenothrin and 49.6 parts of deodorized kerosene are well mixed into a solution. The solution is filled in an aerosol container, followed by the procedures described in Formulation Example 12, to obtain an oil-based aerosol of each compound.

FORMULATION EXAMPLE 18

0.2 Part of each of the present compound (1) to (20), 0.5 part of fenitrothion and 49.3 parts of deodorized kerosene are well mixed into a solution. The solution is filled in an aerosol container, followed by the procedures described in Formulation Example 12, to obtain an oil-based aerosol of each compound.

FORMULATION EXAMPLE 19

0.05 Part of the present compound (4), 0.2 part of tetramethrin, 0.05 part of resmethrin, 7 parts of xylene and 32.7 parts of deodorized kerosene are well mixed into a solution. The solution is filled in an aerosol container, followed by the procedures in Formulation Example 12, to obtain an oil-based aerosol.

FORMULATION EXAMPLE 20

0.4 Part of each of the present compounds (1) to (20), 2 parts of piperonyl butoxide, 11.6 parts of deodorized kerosene and 1 part of emulsifiable agent (manufactured by Atlas Chemical Co., Ltd. under a registered Trade Mark "Atomos 300") are well mixed, and 50 parts of distilled water are added thereto. The resulting emulsion is charged with 35 parts of deodorized butane and deodorized propane (3:1 mixture) into an aerosol container to obtain an water-based aerosol of each compound.

FORMULATION EXAMPLE 21

0.3 Gram of each of the present compounds (1) to (20) is dissolved in 20 ml of methanol. This solution and 99.7 g of a mosquito coil carrier, which is a 3:5:1 mixture of Taba powder, Pyrethrum marc and wood powder, are uniformly mixed with stirring. After evaporating methanol, 150 ml of water is added to the residue, and the mixture is well kneaded, shaped and dried to obtain mosquito coils of each compound.

FORMULATION EXAMPLE 22

0.2 Gram of each of the present compounds (1) to (20) is dissolved in 20 ml of methanol. This solution and 99.8 g of a mosquito coil carrier are mixed, followed by the procedures described in Formulation Example 21, to obtain mosquito coils of each compound.

FORMULATION EXAMPLE 23

0.1 Gram of each of the present compounds (1) to (20) is dissolved in 20 ml of methanol. This solution and 99.9 g of a mosquito coil carrier are mixed, followed by the procedures described in Formulation Example 21, to obtain mosquito coils of each compound.

FORMULATION EXAMPLE 24

0.05 Gram of each of the present compounds (1) to (20) is dissolved in 20 ml of methanol. This solution and 99.95 g of a mosquito coil carrier are mixed, followed by the procedures described in Formulation Example 21, to obtain mosquito coils of each compound.

FORMULATION EXAMPLE 25

0.02 Gram of each of the present compounds (1) to (20), 0.01 g of Yosinox 425 (a registered Trade Mark of Yoshitomi Pharmaceutical Co., Ltd.), 0.07 g of isopropyl myristate and 0.05 g of deodorized kerosene are well mixed to make the premixture solutions of fumigant. A pulp plate having 3.5 cm in length, 2.2 cm in width and 0.28 cm in thickness is impregnated with each solution to obtain an electric heating mat of each compound.

In this formulation, a sheet of asbestos can be used as a carrier instead of the pulp plate.

FORMULATION EXAMPLE 26

0.01 Gram of each of the present compound (1) to (20), 0.01 g of Yosinox 425, 0.08 g of isopropyl myristate and 0.05 g of deodorized kerosene are well mixed, followed by the procedures described in Formulation Example 25, to obtain an electric heating mat of each compound.

In this formulation, a sheet of asbestos can be used as a carrier instead of the pulp plate.

FORMULATION EXAMPLE 27

0.05 Gram of each of the present compounds (1) to (20), 0.01 g of Yosinox 425, 0.04 g of isopropyl myristate and 0.05 g of deodorized kerosene are well mixed to make the premixture solutions of fumigant. A pulp plate having 3.5 cm in length, 2.2 cm in width and 0.11 cm in thickness is impregnated with each solution to obtain an electric heating mat of each compound.

In this formulation, a sheet of asbestos can be used as a carrier instead of the pulp plate.

FORMULATION EXAMPLE 28

0.025 Gram of each of the present compounds (1) to (20), 0.01 g of Yosinox 425, 0.065 g of isopropyl alcohol and 0.05 g of deodorized kerosene are well mixed, followed by the procedures described in Formulation Example 27, to obtain an electric heating mat of each compound.

In this formulation, a sheet of asbestos can be used as a carrier instead of the pulp plate.

FORMULATION EXAMPLE 29

0.1 Gram of each of the present compounds (1) to (20) is dissolved in a proper amount of acetone. A porous ceramic plate having 4.0 cm in square and 1.2 cm in thickness is impregnated with the acetone solution to obtain a heating fumigant of each compound.

FORMULATION EXAMPLE 30

0.02 Gram of each of the present compounds (1) to (20) is dissolved in a proper amount of acetone. A strip of filter paper having 15 cm in length and 2 cm in width is impregnated with each acetone solution to obtain an insecticidal strip of each compound.

FORMULATION EXAMPLE 31

0.2 Gram of each of the present compounds (1) to (20) is dissolved in a proper amount of acetone. A sheet of filter paper having 15 cm in length and 10 cm in width is impregnated with each acetone solution to obtain an insecticidal sheet of each compound.

These preparations are used as they are or as diluted solutions with water. Also, they may be applied in mixture with other insecticides, acaricides, nematocides, fungicides, herbicides, plant growth regulators, fertilizers, soil improvers and the like.

When the present compound is used as an insecticidal composition, its dosage rate is generally 50 to 500 g per ha. When emulsifiable concentrates, wettable powders, etc. are used for controlling agricultural pests as aqueous dilute solutions, the application concentration of the compound is 10 to 1000 ppm. When emulsifiable concentrates, wettable powders, etc. are used for controlling hygienic pests, they are diluted with water to the solutions containing 10 to 10000 ppm of the compound and sprayed. Dusts, granules, oil sprays, aerosols, mosquito coils, electric mats, fumigants, volatile agents, etc. are used as they are without dilution.

Next, test examples will be shown. The present compounds are shown by Compound No. in Table 1, and compounds used as a reference are shown by Compound symbol in Table 2.

TABLE 2

| Symbol | Structure | Name |
|---|---|---|
| (A) | $(CH_3O)_2P(=S)-S-CH(COOC_2H_5)-CH_2COOC_2H_5$ | Malathion |
| (B) | (structure shown) | Compound No. 38 described in Japanese published examined patent application No. 42045/'80 |
| (C) | (structure shown) | Compound No. 74 described in the same patent application as mentioned above |

TABLE 2-continued

| Symbol | Structure | Name |
|---|---|---|
| (D) | [structure diagram] | Allethrin |

TEST EXAMPLE 1

The emulsifiable concentrate of the following present compounds prepared according to Formulation Example 7 were each diluted with water to obtain respective 200 times dilution aqueous solutions (corresponding to 500 ppm).

Two ml of thus diluted solutions were impregnated into 13 g of the artificial diet for tobacco cutworms (*Spodoptera litura*) and thus prepared diet was placed in a polyethylene cup of 11 cm in diameter, respectively. Then, ten 4th instar larvae were released therein.

Six days after, the dead and alive of the larvae were observed to calculate the mortality (two replications).

The results are shown in Table 3.

TABLE 3

| Test compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| (19) | 100 |
| (20) | 100 |
| No treatment | 5 |

TEST EXAMPLE 2

The emulsifiable concentrates of the following present compounds and a reference compound obtained according to Formulation Example 7 were each diluted with water to obtain respective 200 times dilution aqueous solutions [corresponding to 500 ppm), and rice seedlings (about 12 cm in length) were dipped for 1 minute in the resulting aqueous dilute solutions. After air-drying, the seedlings were placed in a test tube, and 10 adults of a resistant strain of green rice leafhopper (*Nephotettix cincticeps*) were liberated in the tube. After one day, the dead and alive of the insects were observed to calculate the mortality (two replications).

The results are shown in Table 4.

TABLE 4

| Test compound | Mortality (%) |
|---|---|
| (1) | 100 |
| (2) | 100 |
| (3) | 100 |
| (4) | 100 |

TABLE 4-continued

| Test compound | Mortality (%) |
|---|---|
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| (19) | 100 |
| (20) | 100 |
| (A) | 50 |
| No treatment | 5 |

TEST EXAMPLE 3

After the following chemical compounds of this invention and reference compounds were dissolved in acetone to prepare solutions with a given concentration, 1 ml of each of the thus prepared solutions was homogeneously applied to the inner bottom surface of a glass petri dish with 9 cm inner diameter and 2 cm height (bottom area, 63.6 cm$^2$). After acetone was evaporated off, the thus treated glass petri dish was put upside down on a nylon gauze (16 mesh) used as a cover of a plastic cup (9 cm in diameter and 4.5 cm height) to which 20 female adults of susceptible houseflies (*Musca domestica*; CSMA strain) had been liberated. As the houseflies were interposed by the nylon gauze, they could not contact the applied surface directly. Sixty minutes after, the number of knocked down adults was counted to calculate KD$_{50}$ value (50% knock down dosage). One-hundred and twenty minutes after, the petri dishes were removed and water and feed were given to the adults. Twenty-four hours after, the dead or alive of the adults were observed to calculate LD$_{50}$ value (50% lethal dose) (two replications).

The results are shown in Table 5.

TABLE 5

| Test compound | KD$_{50}$ value (mg/m$^2$) after 60 minutes | LD$_{50}$ value (mg/m$^2$) after 24 hours |
|---|---|---|
| (1) | 0.55 | 0.37 |
| (2) | 1.1 | 1.3 |
| (3) | 1.5 | 0.53 |
| (4) | 1.0 | 0.78 |
| (5) | 3.3 | 3.9 |
| (6) | 0.95 | 0.74 |
| (7) | 1.1 | 0.77 |
| (8) | 2.3 | 2.7 |
| (9) | 1.9 | 1.3 |
| (10) | 1.4 | 0.93 |
| (11) | 4.7 | 7.1 |
| (12) | 2.5 | 1.7 |
| (13) | 0.44 | 0.30 |
| (14) | 0.53 | 0.23 |

TABLE 5-continued

| Test compound | $KD_{50}$ value (mg/m$^2$) after 60 minutes | $LD_{50}$ value (mg/m$^2$) after 24 hours |
| --- | --- | --- |
| (15) | 2.4 | 0.71 |
| (16) | 0.88 | 1.0 |
| (17) | 0.34 | 0.11 |
| (18) | 1.4 | 0.70 |
| (19) | 5.9 | 0.57 |
| (20) | 2.1 | 0.57 |
| (B) | >50 | ≧50 |
| (C) | >50 | >50 |

TEST EXAMPLE 4

The mosquito coils containing 0.3% and 0.15% of the present compounds or a reference compound were prepared according to the procedures in Formulation Example 21.

Into a 0.34 m$^3$ glass chamber were liberated each of 10 female adults of common mosquitoes (*Culex pipiens pallens*) and 10 adults of houseflies (*Musca domestica*) (♂/♀ = 1/1).

Then 1 g of each of the mosquito coils were ignited on both ends and placed in the chamber.

Thereafter, the number of knocked down insects was counted at various time intervals to calculate $KT_{50}$ value (50% knock-down time) by the probit method (two replications).

The results are shown below.

TABLE 6

| Test compound | $KT_{50}$ value (min) | | | |
| --- | --- | --- | --- | --- |
| | common mosquito | | housefly | |
| | 0.15% | 0.3% | 0.15% | 0.3% |
| (1) | 4.1 | 3.8 | 5.9 | 4.6 |
| (2) | 7.3 | 6.5 | 6.0 | 5.6 |
| (3) | 4.5 | 4.3 | 6.6 | 6.1 |
| (4) | 4.2 | <3.0 | 4.9 | 4.8 |
| (14) | 4.5 | 3.9 | 5.9 | 5.8 |
| (17) | 3.4 | 3.1 | 4.8 | 4.2 |
| (D) | 14 | 11 | 22 | 16 |

What is claimed is:

1. A compound represented by the formula,

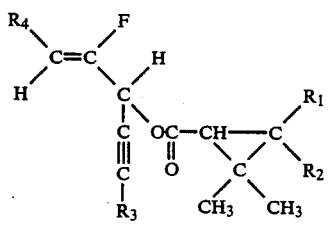

wherein $R_1$ represents a hydrogen atom $R_2$ represents a group of the formula

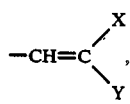

in which X and Y are the same or different and represent a methyl group, a halogen atom or a halogenated lower alkyl group, $R_3$ represents a hydrogen atom and $R_4$ represents a hydrogen atom, a lower alkyl group, a lower alkenyl group or a lower alkynyl group.

2. The compound according to claim 1, wherein $R_1$ represents a hydrogen atom; $R_2$ represents a group of the formula

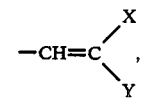

in which X and Y are the same or different represent a methyl group, a halogen atom or a halogenated $C_{1-3}$ alkyl group; $R_3$ represents a hydrogen atom; and $R_4$ represents a hydrogen atom, a $C_{1-5}$ alkyl group, a $C_{2-4}$ alkenyl group or a $C_{2-4}$ alkynyl group.

3. The compound according to claim 2, wherein X and Y are the same or different and represent a methyl group, a chlorine atom, a fluorine atom, a bromine atom or a trifluoromethyl group; and $R_4$ represents a $C_{2-4}$ alkyl group, an allyl group or a propargyl group.

4. The compound according to claim 3, wherein the acid moiety has an absolute configuration of (1R).

5. The compound according to claim 3, wherein $R_4$ represents an ethyl group.

6. The compound according to claim 5, wherein the alcohol moiety has the same absolute configuration as that of the corresponding levo optical rotatory free alcohol.

7. The compound according to claim 6, wherein the acid moiety has an absolute configuration of (1R).

8. A compound of the formula;

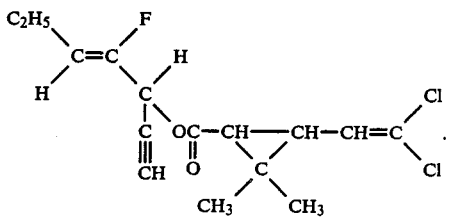

9. The compound according claim 8, wherein the acid moiety has an absolute configuration of (1R)-trans and the alcohol moiety has the same absolute configuration as that of corresponding levo optical rotatory free alcohol.

10. A compound of the formula,

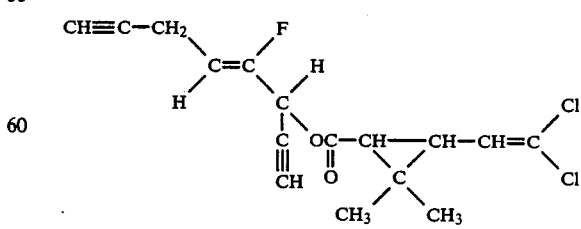

in which the acid moiety has an absolute configuration of (1R)-trans.

11. A compound of the formula,

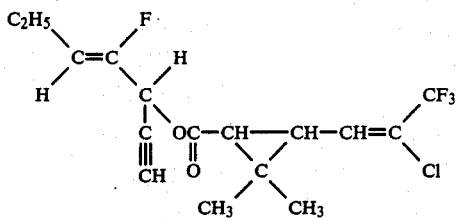

in which the acid moiety has an absolute configuration of (1RS)-cis.

12. A compound of the formula,

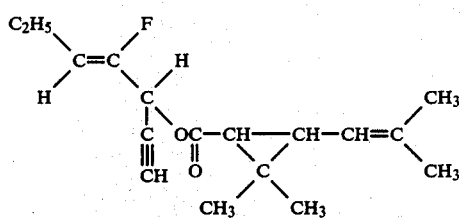

in which the acid moiety has an absolute configuration of (1R)-trans.

13. A compound of the formula,

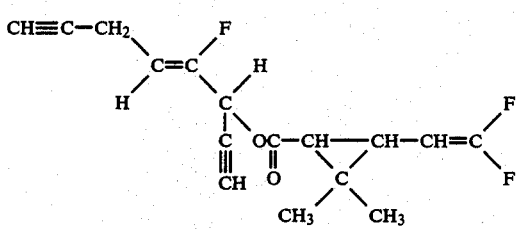

in which the acid moiety has an absolute configuration of (1R)-trans.

14. A compound of the formula,

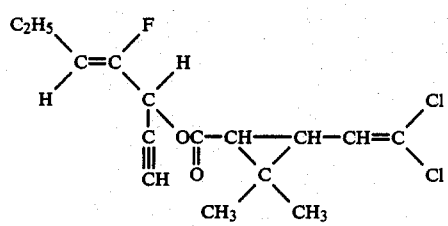

in which the acid moiety has an absolute configuration of (1R)-trans.

15. An insecticidal composition which comprises as an active ingredient an insecticidally effective amount of a compound represented by the formula,

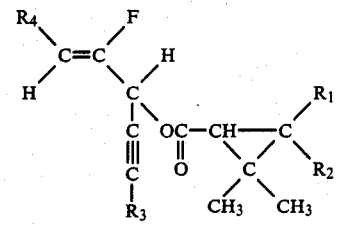

wherein $R_1$ represents a hydrogen atom; $R_2$ represents a group of the formula

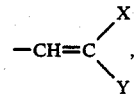

in which X and Y are the same or different and represent a methyl group, a halogen atom or a halogenated lower alkyl group, $R_3$ represents hydrogen atom; and $R_4$ represents a hydrogen atom, a lower alkyl group, a lower alkenyl group or a lower alkynyl group, and an inert carrier.

16. The insecticidal composition according to claim 15, wherein $R_1$ represents a hydrogen atom; $R_2$ represents a group of the formula

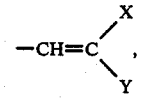

in which X and Y are the same or different represent a methyl group, a halogen atom or a halogenated $C_{1-3}$ alkyl group; $R_3$ represents a hydrogen atom; and $R_4$ represents a hydrogen atom, a $C_{1-5}$ alkyl group, a $C_{2-4}$ alkenyl group or a $C_{2-4}$ alkynyl group.

17. The insecticidal composition according to claim 16, wherein X and Y are the same or different and represent a methyl group, a chlorine atom, a fluorine atom, a bromine atom or a trifluoromethyl group; and $R_4$ represents a $C_{2-4}$ alkyl group, an allyl group or a propargyl group.

18. The insecticidal composition according to claim 17, wherein the acid moiety has an absolute configuration of (1R).

19. The insecticidal composition according to claim 17, wherein $R_4$ represents an ethyl group.

20. The insecticidal composition according to claim 19, wherein the alcohol moiety has the same absolute configuration as that of the corresponding levo optical rotatory free alcohol.

21. The insecticidal composition according to claim 20, wherein the acid moiety has an absolute configuration of (1R).

22. A method for controlling an insect which comprises applying an insecticidally effective amount of the compound according to claim 1 to the insect.

* * * * *